(12) United States Patent
Song

(10) Patent No.: US 9,555,147 B2
(45) Date of Patent: Jan. 31, 2017

(54) AQUEOUS-TRIGGERED COLOR-APPEARING INKS

(71) Applicant: Kimberly-Clark Worldwide, Inc., Neenah, WI (US)

(72) Inventor: Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 431 days.

(21) Appl. No.: 14/224,261

(22) Filed: Mar. 25, 2014

(65) Prior Publication Data

US 2014/0207095 A1    Jul. 24, 2014

Related U.S. Application Data

(63) Continuation of application No. 12/637,217, filed on Dec. 14, 2009, now Pat. No. 8,697,003.

(51) Int. Cl.
A61F 13/42 (2006.01)
A61L 15/22 (2006.01)
A61L 15/56 (2006.01)
C09B 67/28 (2006.01)
C09B 67/30 (2006.01)

(52) U.S. Cl.
CPC .............. *A61L 15/225* (2013.01); *A61F 13/42* (2013.01); *A61L 15/56* (2013.01); *C09B 67/0077* (2013.01); *C09B 67/0078* (2013.01)

(58) Field of Classification Search
CPC ................................. A61F 13/42; A61L 15/56
USPC ........................................................ 604/361
See application file for complete search history.

(56) References Cited

U.S. PATENT DOCUMENTS

| 4,287,153 A * | 9/1981 | Towsend ........... A61F 13/00008 422/412 |
| 5,017,226 A | 5/1991 | Kulisz |
| 5,096,813 A * | 3/1992 | Krumhar .............. B65D 55/026 422/401 |
| 5,130,290 A | 7/1992 | Tanimoto |
| 5,169,826 A | 12/1992 | Seitz et al. |

(Continued)

FOREIGN PATENT DOCUMENTS

| CN | 85 1 09698 A | 8/1986 |
| CN | 1093096 A | 10/1994 |

(Continued)

*Primary Examiner* — Susan Su
(74) *Attorney, Agent, or Firm* — Kimberly-Clark Worldwide, Inc.

(57) ABSTRACT

The invention describes a color-developing composition that contains at least four major components: (1) a leuco dye or a combination of leuco dyes, (2) an electron-withdrawing color-developer agent or a combination of color-developers that can form colored complexes with the leuco dyes, (3) a separator or combination of separators that when present in sufficient amounts, can prevent the formation of the colored complexes between the color-developer and leuco dyes, all contained within (4) an encapsulation matrix that includes at least one film-forming and one aqueous-insoluble polymer. All of the foregoing components are dissolved together in a volatile organic solvent medium to form a homogeneous solution that can be applied as an ink on substrates, which can be incorporated as part of absorbent articles or personal care products.

11 Claims, 2 Drawing Sheets

(56) References Cited

U.S. PATENT DOCUMENTS

| | | | |
|---|---|---|---|
| 5,197,958 A * | 3/1993 | Howell | A61F 13/42 |
| | | | 604/361 |
| 5,215,956 A | 6/1993 | Kawashima | |
| 5,415,434 A | 5/1995 | Kawashima | |
| 5,443,629 A | 8/1995 | Saville et al. | |
| 5,466,653 A | 11/1995 | Ma et al. | |
| 5,476,540 A | 12/1995 | Shields et al. | |
| 5,478,382 A | 12/1995 | Miller et al. | |
| 5,485,792 A | 1/1996 | Keyser et al. | |
| 5,536,696 A | 7/1996 | Horsten et al. | |
| 5,792,863 A | 8/1998 | Ohashi et al. | |
| 5,948,512 A | 9/1999 | Kubota et al. | |
| 6,103,301 A | 8/2000 | Iori et al. | |
| 6,161,929 A | 12/2000 | Erdtmann et al. | |
| 6,293,667 B1 | 9/2001 | Gregory et al. | |
| 6,341,856 B1 | 1/2002 | Thompson et al. | |
| 6,793,721 B2 | 9/2004 | Shen et al. | |
| 7,087,265 B1 | 8/2006 | Netsch | |
| 7,333,126 B2 | 2/2008 | Taugher et al. | |
| 8,187,892 B2 | 5/2012 | Ribi | |
| 2002/0018188 A1 * | 2/2002 | Mori | G03D 13/002 |
| | | | 355/18 |
| 2003/0206940 A1 * | 11/2003 | Gott | A61K 8/0208 |
| | | | 424/443 |
| 2005/0120919 A1 | 6/2005 | Davies-Smith et al. | |
| 2005/0287356 A1 | 12/2005 | Li et al. | |
| 2006/0069362 A1 * | 3/2006 | Odorzynski | A61F 13/42 |
| | | | 604/361 |
| 2006/0142156 A1 | 6/2006 | Filosa et al. | |
| 2007/0012218 A1 | 1/2007 | Jang et al. | |
| 2007/0017413 A1 | 1/2007 | Kwan et al. | |
| 2007/0287989 A1 * | 12/2007 | Crawford | A61M 39/045 |
| | | | 604/507 |
| 2008/0145948 A1 | 6/2008 | Menon | |
| 2011/0152805 A1 | 6/2011 | Gil | |

FOREIGN PATENT DOCUMENTS

| | | |
|---|---|---|
| CN | 1239123 A | 12/1999 |
| CN | 1427046 A | 7/2003 |
| EP | 0 980 028 A1 | 2/2000 |
| EP | 1 719 634 B1 | 3/2009 |
| EP | 2 067 458 A1 | 6/2009 |
| WO | WO 2007/004629 A1 | 1/2007 |

* cited by examiner

AQUEOUS-TRIGGERED COLOR-APPEARING INKS

CROSS-REFERENCE TO RELATED APPLICATION

This application is a divisional of U.S. patent application Ser. No. 12/637,217, filed Dec. 14, 2009. U.S. patent application Ser. No. 12/637,217 is incorporated by reference herein in its entirety.

FIELD OF INVENTION

The present invention pertains to an indicating composition for an aqueous medium. In particular, the present invention describes a medium or ink that can change from being colorless to color in the presence of an aqueous solution.

BACKGROUND

Many products, including consumer, health care, and professional products, are more effectively used by an end user when the product includes a feature that can communicate or signal to the user a particular condition or indicate the relative level or degree of use. An example is a visual indicator that causes the product to change color or appearance. Color indicators can either indicate a change in condition or a degree of use through a change from "no color" to "color" (or vice versa) or through a change from one color to a different color.

Exemplary conditions that could be monitored using a color indicator include physical conditions such as the presence of moisture and chemical conditions such as a change in pH. Exemplary consumer products that could be more effective and deliver more benefits to end users by incorporating a suitable color indicator include absorbent articles, facial tissues, bath tissue, paper towels, household cleaning items and personal cleaning wipes. Exemplary professional products that could be more effective and deliver more benefits to end users by incorporating a suitable color indicator include products for medical use, safety garments, industrial cleaning products and nonwoven materials.

Color indicators are well known and are available in various forms. Desirable performance attributes include durability and good retention (i.e. the color indicator remains where intended and does not leach out into other components of the product within which it is being used). Depending on the product application, it may also be desirable to have the structure in which the color indicator is used to be wettable, but water insoluble. For purposes of applying the color indicator to a component of a product, it may also be desirable to have a color indicator that can be applied in liquid form at room temperature. When the color indicator is in a liquid form at room temperature, the color indicator can be printed (just like an ink composition) onto the desired component of a product.

Examples of the color indicators that have been already incorporated into consumer products include diapers that have wetness sensors. Some of the wetness sensors used in diapers change color to indicate wetness while others lose color in response to wetness (i.e. the color fades or disappears when it is dissolved by water). The concept of incorporating a color-changing composition into a wearable article (such as a disposable diaper) is known in the art. For example, U.S. Pat. No. 7,159,532 issued to Klofta et al. (hereinafter "the '532 patent") is directed to wetness indicating compositions having improved colorant retention and durability for use with wearable articles. The wetness indicating compositions of the '532 patent have a first binding agent and a second binding agent. The first binding agent immobilizes a colorant when the colorant is in its initial color state and the second binding agent immobilizes the colorant when the colorant is in its final color state. The component materials used in the examples provided in the '532 patent are solid at room temperature as indicated by the description that they need to be melted by heating in order to combine them. While the wetness indicating compositions of the '532 patent are capable of changing color in response to a stimulus, they are not capable of being applied to an article in liquid form at room temperature.

While the color-changing compositions known in the art provide certain benefits, there remains a need for a film-forming composition that can be applied to a substrate. There also remains a need for a composition that is durable, has good retention and that shows rapid and dramatic color change when the composition is used in a product. When the purpose of the composition is to detect the presence of wetness, there remains a need for a composition that is water-resistant and water-insoluble. Further, there remains a need for a composition that can be applied, such as by printing, at room temperature so that the composition can be applied to a substrate without heating.

SUMMARY OF THE INVENTION

The present invention relates in part to a color-developing composition or molecular system for use in an indicator medium or ink solution. The color-developing composition in ink form can form thin films of various patterns and shapes on a substrate upon drying and the films can generate color upon contact with an aqueous medium. The solution composition or molecular system includes at least four-components all dissolved in a volatile organic solvent medium. The four components are an assembly of: 1) a leuco dye or a combination of leuco dyes, 2) an electron-withdrawing color developer or a combination of color-developers that can form color complexes when associated with the leuco dye under the proper conditions, and 3) a separator or combination of separators, which when dissolved in the system in an adequate quantity, can prevent the formation of the colored complexes, all contained within 4) an polymeric encapsulation matrix. The encapsulation matrix is composed of at least a film-forming and water insoluble polymer. The composition may be part of an indicator medium that is an organic solvent-based wetness ink. The ink in its original state is colorless and the films formed from the inks upon evaporation of the organic solvents are also colorless because no water is present in the original solution to interact with the components. The presence or introduction of water to the dried films will activate the composition to trigger color manifestation. The present invention belongs to a class of organic-solvent based wetness indicating inks that can form thin films on various substrates when dried, and the films can achieve rapid and dramatic color appearing upon wetting, such as when in contact with an aqueous-based fluid like urine. The inks can be applied to various substrates such as polyethylene films by means of various techniques such as flexographic and gravure printing.

In another aspect, the invention is a colorless or pale-colored, non-aqueous-based, homogeneous solution having a composition comprising: a) one or more leuco dyes; b) one or more separators or desensitizers that are non-volatile and are significantly soluble in both volatile organic solvents and water; c) one or more electron withdrawing color-developers that cannot form colored complexes with said leuco dyes in the presence of a significant amount of the separators without the presence of water, but can form colored complexes with the leuco dyes in the presence of water, wherein said composition is in an encapsulation matrix that is insoluble in water, but soluble in volatile organic solvents. The composition may also include one or more volatile organic solvents.

In yet another aspect, the invention is related to an indicator or a device for wetness sensor that has a solid surface to which the homogeneous solution can be applied or printed.

Further, the invention also relates to an absorbent article that incorporates at least one component that has the homogeneous solution applied or printed on it.

Additional features and advantages of the present molecular system and homogeneous composition will be described in the following detailed description. It is understood that the foregoing general description and the following details description and examples are merely representative of the invention, and are intended to provide an overview for understanding the invention as claimed.

BRIEF DESCRIPTION OF FIGURES

FIG. 3A shows the substrate at an initial stage with a largely colorless appearance. FIG. 3B show the same substrate immediately after an aqueous solution is applied to the ink-printed region of the substrate. FIG. 3C shows the development of color as the aqueous solution more fully reacts with the molecular system in the ink composition.

DETAILED DESCRIPTION OF THE INVENTION

The present invention relates in part to a homogeneous solution having a composition that includes multiple-components. The homogenous solution can be applied as an ink material, by means of conventional printing techniques, to a substrate surface and can form part of a film layer on the substrate. The composition can be applied as a single-phase solution that solidifies into a thin, self-assembled film or matrix upon evaporation of solvents. The film layer includes a color-developing composition that can cause the film layer to change from a largely colorless or pale appearance to a visually distinct or vibrant color when the film layer is exposed to a change in its immediate physical or chemical environment as a result of the introduction of an aqueous medium or mixture.

Section I—Color-Developing Composition or Molecular System

The present invention involves a color-developing composition or molecular system that contains at least four major components: (1) a leuco dye or a combination of leuco dyes, (2) an electron-withdrawing color-developer agent or a combination of color-developers that can form colored complexes with the leuco dyes, (3) a separator or combination of separators that when present in sufficient amounts in the system, can prevent the formation of the colored complexes between the color-developer and leuco dyes, all contained within (4) an encapsulation matrix that includes at least one film-forming and one aqueous-insoluble polymer. The encapsulating matrix contains at least one kind of polymeric resin that can form a thin film on plastic substrate surfaces with good adhesion. All of the foregoing components are dissolved together in a volatile organic solvent medium to form a homogeneous solution. The leuco dye, color-developing agent and separator components are not phase-separated from each other in the solution.

In addition to the four main components, the solution may also contain other additives to adjust their physical properties. The composition may contain reagents to adjust the viscosity of the solution, or may include chemicals to improve adhesion of the composition to certain substrate surfaces upon drying. The composition may also have chemicals that tailor the composition's subsequent wettability on the substrate surface.

Figure 1:
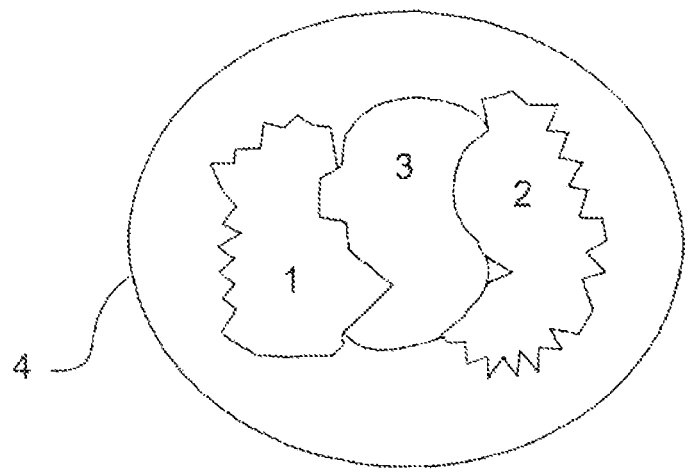
FIG. 1 is a schematic representation of the initial relationship of the three components (leuco dye, electron-withdrawing developer, and separator or desensitizer agent) in the molecular system according to the present invention, and how the three components of the molecular system function with each other when encapsulated.

FIG. 1, is a schematic representation of the initial relationship of the components within the polymeric encapsulation matrix. The leuco dye 1 and color-developer agent 2 are separated from reacting with each other by the separator 3 within the encapsulation 4. The leuco dye and color-developer agent used in the composition exhibit good solubility in organic solvents, but poor solubility in aqueous media. On the other hand, the separator exhibit good solubility in both an aqueous and organic solvent.

Figure 2:
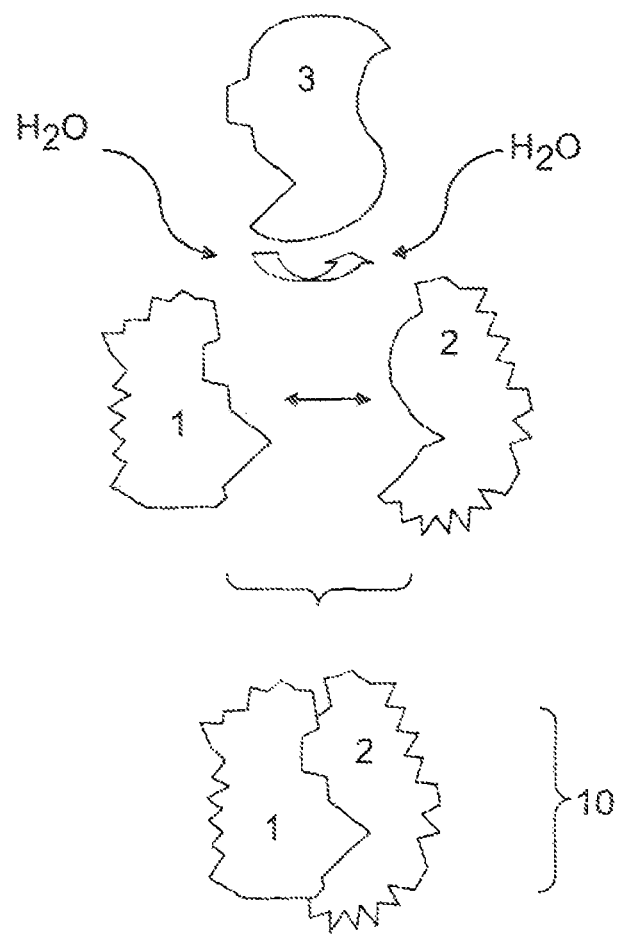
FIG. 2 is a schematic illustration of how the three components in the molecular system interact to develop color from an initial colorless appearance when exposed to an aqueous solution or solvent.

Although not bound by theory, FIG. 2, is a theoretical, schematic illustration of how between the individual components interact with each other to develop color. It is speculated that the leuco dye 1 and the color-developer agent 2 are separated from each other by the separator 3 when the composition is dried by means of solvent evaporation on a substrate to show a colorless or a pale, weakly colored state. The leuco dye and color-developer are capable of interacting to manifest color when the separator dissolves or disperses in the presence of an aqueous solution. Upon wetting or when the liquid pervious encapsulation matrix encounters an aqueous-based solution, the fluid enters the capsule 4. Some of the separator 3 is either dissolved or dissociated from the complex into the aqueous medium.

The water molecules penetrate into the encapsulation to make the micro-environment more hydrophilic. This event permits the other two other components, leuco dyes molecules 1 to interact with the color-developer agent 2 to form colored complexes 10.

Leuco dyes are generally referred to as colorless or pale-colored basic dyes, because the dye molecules can acquire two forms, one of which is colorless. Although not intended to be bound by theory, it is believed that the color-developer agent functions as a Lewis acid, which withdraws electrons from the leuco dye molecule to generate a conjugated system. Hence, the leuco dye appears to manifest color from an originally colorless state.

For example, the spiro form of an oxazine is a colorless leuco dye; the conjugated system of the oxazine and another aromatic part of the molecule is separated by an $sp^3$- hybridized "spiro" carbon. After protonating a part of the molecule, irradiation with UV-light or introducing other kind of such change, the bond between the spiro carbon and the oxazine interrupts, the ring opens, the spiro carbon achieves sp$^2$ hybridization and becomes planar, the aromatic group rotates, aligns its Tr-orbitals with the rest of the molecule, and a conjugated system forms, with ability to absorb photons of visible light, and therefore appear colorful.

The leuco dyes that may be employed can be selected from a variety of dyes including, for example, phthalide leuco dyes, triarylmethane leuco dyes, and fluoran leuco dyes. Examples may include (1) Triarylmethane-based dyes, e.g. 3,3-bis(p-dimethylaminophenyl)-6-dimethylaminophthalide, 3,3-bis(p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl) phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-p-dimethylaminophenyl-3-(1-methylpyrrol-3-yl)-6-dimethylaminophthalide, etc. (2) Diphenylmethane-based dyes, e.g., 4,4'-bisdimethylaminobenzhydryl benzyl ether, N-halophenylleucoauramine, N-2,4,5-trichlorophenyl-leucoauramine, etc. (3) Lactam-based dyes, e.g., rhodamine-B-anilinolactam, rhodamine-(p-nitroanilino)lactam, rhodamine-(o-chloroanilino)lactam, etc. (4) Fluoran-based dyes, e.g., 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-(N-ethyl-p-toluidino)-7-methylfluoran, 3-diethylamino-7-(N-acetyl-N-methylamino)fluoran, fluoran, 3-diethylamino-7-(N-methylamino)fluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino) fluoran, 3-diethylamino-6-methyl-7-phenylaminofluoran, 3-dibutylamino-6-methyl-7-phenylaminofluoran, 3-diethylamino-7-(2-carbomethoxyphenylamino) fluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-(2,4-dimethylamino)fluoran, 3-diethylamino-7-(o-chlorophenylamino)fluoran, 3-dibutylamino-7-(o-chlorophenylamino)fluoran, 3-pyrrolidino-6-methyl-7-(p-butylphenylamino) fluoran, 3-(N-methyl-N-n-amylamino)-6-methyl-7-phenylaminofluoran, 3-(N-ethyl-N-n-amylamino)-6-methyl-7-phenylaminofluoran, 3-(N-ethyl-N-isoamylamino)-6-methyl-7-phenylaminofuluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-β-ethylhexylamino)-6-methyl-7-phenylaminofluoran, etc. The basic dyes useful in this invention are not limited to those exemplified above, and at least two of them can be used in admixture.

The separator or desensitizer can be any of known component agent which exhibit good solubility in both water and organic solvents. Generally, the separators are preferred to be neutral molecules that are without a charge, such as polyalkylene glycol of <1000 Daltons, polyalkylene oxide of <10000 Daltons, block copolymers of polyoxyehtylene polyoxypropylene glycol, polyoxyehtylene nonylphenyl ether, polyoxyethylene distyrenated phenyl ether, neutral surfactants. Other examples of such separators may include glycerin; dodecylamine; 2,4,4-trimethyl-2-oxazoline; polyolefin glycols such as polyethylene glycol, polypropylene glycol and copolymer of ethylene glycol and propylene glycol; polyoxyethylene lauryl ether, polyoxyethylene oleyl ether, polyoxyethylene nonyl phenyl ether, polyoxyethylene sorbitan monolaurate, polyethylene glycol monostearate.

Generally, the color-developers exhibit good solubility in organic solvents. Examples of suitable developers include bisphenol A, zinc chloride, zinc salicylate, and phenol resins. Other examples of color developing materials to be used conjointly with the lecuo dyes may include: 4-tert-butylphenol, α-naphthol, β-naphthol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'-cyclohexylidene diphenol, 4,4-dihydroxy diphenylsulfide, 4,4'-thiobis(6-tert-butyl-3-methyl-phenol), 4,4'-dihydroxydiphenyl sulfone, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, novolak type phenol resins, phenol polymers and like phenol compounds.

Wetness indicating inks from colorless to various colors have been highly desirable for a variety of personal care and health care-related uses, for instance, personal care products such as diapers or adult incontinence articles. However, no practical wetness indicating inks are commercially available. Unlike some water-sensitive coloring sheets, such as described in U.S. Pat. No. 5,130,290, relating to a water-based wetness indicating compositions that are suspensions and not homogenous solutions on paper or pulp-fiber based substrates, the present composition is solution-based and homogeneous. The composition described by the '290 patent is water-based and requires heat-drying. The compositions are suspension and inhomogeneous, not a solution-based ink.

The present composition can be incorporated as part of an organic solvent-based wetness indicating ink. All the components in the inks are soluble in an organic solvent or a mixing organic solvent system and the inks are homogeneous. The ink can induce a dramatic visual appearance change in color in the range of ΔE values of at least 5 or 10, to about 20-40-60. Typically, depending on the active component concentration and amount of urine or other liquid disruption, the color will be eliminated within well under 5 or 10 minutes. According to certain examples the color is discharged within about 6 minutes, or for faster action within about 3 minutes after application of the composition to a stain. One can observe that the color of the discoloration or stain is reduced by ≥5. In certain other embodiments, the observable color of the stain is reduced by at least a ΔE value of 15 or 20, which lightens the stain to being virtually imperceptible by the naked eye. Typically, the discoloration or stain can be reduced by a ΔE value of about 25-40, desirably up to about 50 to 70 or 80. As will be described in further detail, ΔE is the measurement of color change as defined by 3D color space measurements.

Section II—Molecular System Encapsulate

According to the present invention, the composition also includes a water pervious organic polymeric cage or matrix that encapsulates the molecular system. The encapsulation matrix contains at least one polymer that is soluble in organic solvents, but is not well adapted or soluble in aqueous media. The polymers can be a copolymer, block copolymer, linear polymer or random copolymer, or combinations thereof. The polymers can be natural polymers, synthetic polymers, and hybrid polymers of the two. The encapsulation matrix should be able to form stable films on various substrates upon drying, particularly after air drying.

Examples of suitable polymers may include, for instance, Gantrez series polymers from International Specialty Products, Inc., Dermacryl 97 from National Starch, and Amphomers from Akzo Nobel. The encapsulation matrix may also be a mixture of various chemicals dissolved in an organic solvent system. Examples of such a system may include organic solvent-based varnishes, such as varnishes made by Sunchemical Co. Examples of polymers and copolymers that are substantially soluble in organic solvents may include: styrene-butadiene copolymers, acrylic acid ester polymers, polyvinyl acetates, polyvinyl chlorides; polyvinylbutyral, polyvinyl acetate, vinyl chloride-vinyl acetate copolymer, acrylic resin, styrene resin, polyester resin, and polyvinyl acetate, vinyl chloridevinyl acetate copolymer, styrene-maleic anhydride copolymer, isobutylene-maleic anhydride copolymer, polyvinyl butyral.

According to the invention, the composition also contains a volatile organic solvent system. Examples of such volatile organic solvents or a mixing solvent system may include low-molecular weight alcohols, such as butanol, ethanol, propanol, and acetone or tetrahydrofuran or their mixtures.

Section III—Ink Medium

As stated before, the invention involves a colorless or pale-colored, non-aqueous-based, homogeneous solution having a composition comprising: a) one or more leuco dyes; b) one or more separators or desensitizers that are non-volatile and are significantly soluble in both volatile organic solvents and water; c) one or more electron withdrawing color-developers that cannot form colored complexes with said leuco dyes in the presence of a significant amount of said separators without the presence of water, but can form colored complexes with the leuco dyes in the presence of water, wherein said composition is in an encapsulation matrix that is insoluble in water, but soluble in volatile organic solvents. The composition may include one or more volatile organic solvents.

The volatile organic solvents may include, for example, ethanol, methanol, propanol, isopropanol, butanol, acetone, tetrahydrofuran (THF), benzene and toluene, methylene chloride, chloroform, or combinations thereof.

In another aspect of the present invention, the encapsulated color-developing component molecular system can be mixed into a homogeneous solution to form an ink. The ink can be applied to the surface of plastic substrates, such as polyethylene, polypropylene, or other polyolefins.

The ink has a composition of a volatile organic-based solvent or a mixture of different volatile organic solvents, a immobilization composition that includes at least one organic soluble but water insoluble film forming polymer or copolymer, a leuco dye and a color-developer agent both of which are soluble only in organic solvent, and a separator that are soluble in both organic solvent and water. The ink is originally colorless in the absence of water, and manifests color when water is present.

The leuco dyes can be present in the composition from about 0.01 wt. % to about 10 wt. %. Typically the amount of leuco dye can be between about 0.05 or 0.1 wt. % to about 4 or 5 wt. %, or 6 or 7 wt. %; desirably the range is between about 0.5 or 1 wt. % to about 2.5, 3 or 5 wt. %, inclusive. The amount of separators typically are present from about 1 wt. % to about 20 wt. % or 25 wt. %. Alternatively, the separators can be present from about 1.5, 2, or 3 wt. % to about 15, 17, or 18 wt. %, inclusive. The amount of developers that are present can range from about 0.5 wt. % or 1 wt. % to about 10 wt. % or 12 wt. %; typically, between about 1 or 2 wt % to about 7, 8 or 10 wt %. The polymeric resin in the encapsulation matrix is present from about 10 wt. % to about 80 wt. %. Typically, the amount of polymer resin is between about 12, 15, or 20 wt % to about 65, 70, or 78 wt. %, inclusive. The volatile organic solvents can be present from about 20 wt. % to about 90 wt. %; typically between about 25, 30, or 35 wt % to about 80, 85, or 88 wt %, inclusive.

Section IV—Printed Articles

The homogeneous wetness inks can be printed on various material substrates, such as plastics, polyethylene or polypropylene films, or cellulose-based papers and tissues. The inks can be air-dried to show a colorless or nearly colorless state of appearance (i.e., either no color or very weak background shade). The dried inks show various colors upon being wetted depending on the kind of leuco dye used. For example, the film layer may be on a nonwoven material that is used as a component of an absorbent article.

The water-insoluble, film-forming polymer and the other components of the color-changing composition can be dissolved in the organic solvent prior to application onto the substrate. When the mixture of the color-changing composition and the organic solvent is formed, the mixture is liquid at room temperature. The volatile organic solvent evaporates when the color-changing composition is either applied to the film layer or forms the film layer. Suitable water-insoluble, film-forming polymers include acrylate/acrylamide copolymers, polyurethane adhesives, copolymers of vinylpyrrolidone and copolymers of dimethyl aminopropyl methacrylamide. Commercially-available suitable polymers include DERMACRYL 79 polymer and AMPHOMER HC polymer, both of which are acrylate/octylacrylamide copolymers available from Akzo Nobel. Another example of a commercially-available suitable polymer is GANTREZ SP polymer, which is a mono-alkyl ester of poly(methyl vinyl ether/maleic acid) copolymer available from International Specialty Products, Inc. The color-changing compositions of the invention include a water-insoluble, film-forming polymer in an amount of from 20% to 95% of the total weight of the color-changing composition. Desirably, the color-changing compositions of the invention include a water-insoluble, film-forming polymer in an amount of from 60% to 90% of the total weight of the color-changing composition.

Once the homogeneous solution are printed and dried on the surface of the substrate, the dried solution can form thin films that can manifest color when they contact a water-containing medium. According to certain embodiments, it is desirably that the thin films either cover or form a pattern on a visually perceivable surface of the substrate. This feature would be useful when the printed substrate is part of either an absorbent article or a personal care product formed with the substrate that may contact an aqueous solution or urine. The absorbent article may for example be a diaper, feminine hygiene pad, adult incontinence article, or wiper cloth.

The article may comprise a polymeric film or nonwoven substrate surface having at least a portion of said substrate surface printed with a color-developing medium that contains a complex formed from a leuco dye, a electron-withdrawing color-developer agent, and a separator, all contained within an aqueous-pervious polymeric matrix, where said separator is soluble in both an aqueous and organic solvent, and said leuco dye and color-developer are capable of interacting to manifest color when said separator dissolves or disperses in the presence of an aqueous solution. The substrate can be either a porous film or non-porous film, or a combination of both kinds of films. The porous films may include cellulose based tissue, papers, nonwoven materials, or breathable films, such as polyethylene and polypropylene films imbedded with calcium carbonate.

Figure 3A:
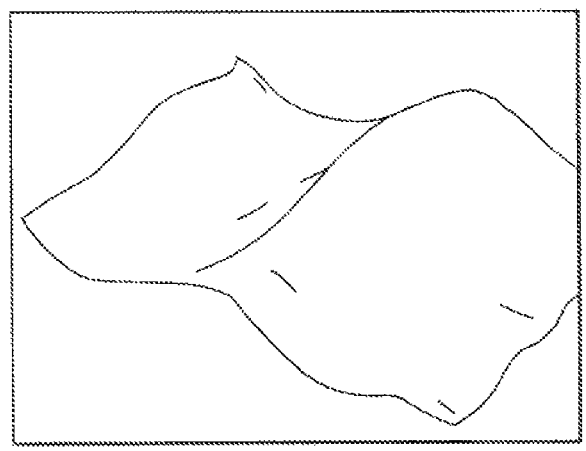
FIG. 3A-3C is a series of illustrations of a polymeric film or nonwoven fabric or web substrate that is printed with an ink composition containing the present molecular system.
Figure 3B:
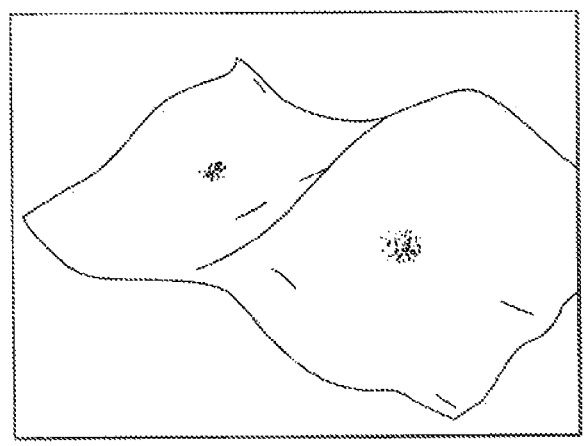
Figure 3C:
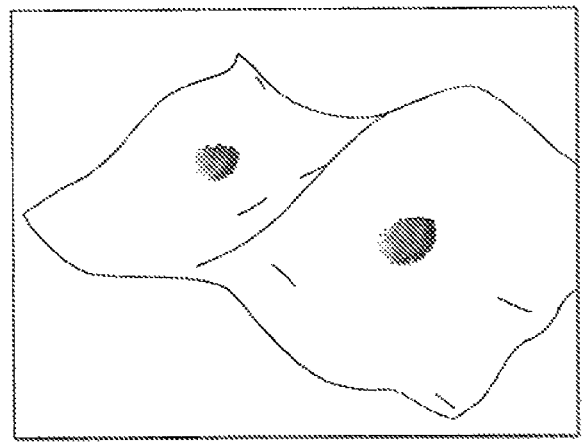

FIGS. 3A-3C are illustrations that show a substrate surface, which may be either porous or non-porous, polymeric or cellulose-based, that has been printed with ink according to the present invention. FIG. 3A shows the substrate at an initial stage with a largely colorless appearance. FIG. 3B shows the same substrate immediately after the printed area contacts an aqueous-based fluid. FIG. 3B shows the further development of color as either more aqueous-based fluid is applied or spreads more fully over the printed area, and interacts with the present color-developing composition.

Section V.—Empirical

Example 1

To each of six glass vials (labeled as vial 1, 2, 3, 4, and 5, respectively) was added with 500 ul of crystal violet lactone (12 mg/ml) in ethanol and 500 ul of biphenol A (50 mg/ml) in ethanol. A different amount of polyethylene glycol (PEG, MW: 200), ranging from 18, 30, 60, 120 and 18 mg, was added to vial 1, 2, 3, 4 and 5, respectively. To each of the vials was further added 2 ml Varnish from Sunchemical Co. and the mixtures were vortexed for 2 minutes. To vial 6, 100 ul of benzethenium chloride in ethanol (50 mg/ml) was added and mixed well. The mixture in each vial was used to form a thin film on a polyethylene film using a brush and the thin film was then air-dried for 4 hours. The color of the film from each vial is slightly blue, slightly blue, colorless, colorless and blue for vial 1, 2, 3, 4, and 5, respectively. Upon wetting with water or synthetic urine, all the films became blue within 5 minutes.

Example 2

The ink from vial 4 in example 1 was applied to printer-copy paper from XEROX, KLEENEX®-brand tissue from Kimberly-Clark and were air-dried for 5 hours. The color of the paper and tissue was white. The paper and tissue became blue upon in contact with water or synthetic urine.

Example 3

About 25 mg zinc salicylate and 120 mg polyethylene glycol (molecular weight: 200) were added to 500 ul of crystal violet lactone (12 mg/ml) in ethanol. The mixture was blue. 1 ml varnish was added and the color remains blue. The ink was brusheded on polyethylene film and air-dried. The dried film remains blue. No color change was observed upon in contact with water or synthetic urine. Using 25 mg benzethenium chloride to replace the PEG makes the ink even more blue.

Example 4

About 1 ml crystal violet lactone (20 mg/ml) in acetone was mixed with 500 ul of benzethenium chloride in ethanol (50 mg/ml). 1 ml SUnchemical's varnish was added and mixed to make an ink. The ink was brushed on polyethylene film to form a thin film. The thin film was dried and show weak blue color. The weak blue color became deep blue upon wetting with water or synthetic urine.

Example 5

About 6 mg crystal violet lactone, 18 mg biphenol A and 72 mg Tween 20 were dissolved in 1 ml ethanol. 1 ml Sunchemical varnish was added to the solution and mixed well. The solution was brushed on polyethylene film and air dried. The film shows white. The white color did not change upon contact with water or synthetic urine.

Example 6

About 250 ul crystal violet lactone (24 mg/ml in acetone) was mixed with biphenol A in ethanol (50 mg/ml). 250 µl Sunchemical varnish and 500 µl PEG (75 mg/ml, MW: 1000) in acetone were added and mixed. The solution was brushed on polyethylene film and showed no color upon air-drying. The film has no significant color change upon wetting with water or synthetic urine. Using PEG (MW: 5000) to replace PEG (MW: 100) results in the film that did not change color upon wetting.

Example 7

About 500 µl crystal violet lactone (24 mg/ml) in acetone, 500 µl zinc salicylate (100 mg/ml) in ethanol and 1 ml varnish were mixed well. The mixture was equally divided into four portions, each in a vial, designated as vial 1, 2, 3, and 4, respectively. To vial 1, 2, 3 and 4 was added 0, 100 µl, 200 µl and 400 µl of benzenthenium chloride (50 mg/ml) in isopropanol, respectively. The mixture in each vial was brushed on polyethylene film and air-dried. The film color made of the mixture from vial 1, 2, 3 and 4 is deep blue, deep blue, moderately blue and weak blue, respectively. Upon wetting with water or synthetic urine, the color remains the same for the samples from Vial 1 and 2. Slightly discoloring was observed for the film from Vial 3. Significantly discoloring was observed for the sample from Vial 4.

Example 8

About 500 µl crystal violet lactone (24 mg/ml) in ethanol, 500 µl biphenol A (50 mg/ml) in ethanol and 60 ul PEG (MW: 200) were mixed well. 1 ml Sunchemical varnish was added and mixed well. The mixture was applied to an outer cover film with a spunbond layer and air-dried to show a slightly blue color. The piece was used to cover a rectangular hole cut from a new-born diaper on the outer cover. The ink film was in contact with the superabsorbent core through tapes. 10 ml of synthetic urine added to the diapers in the center causes the film to change to deep blue.

Example 9

About 500 µl ORC Red KC from Organic Dyestuff Co. (16 mg/ml) in acetone and 500 ul diphenol A (50 mg/ml) in ethanol was mixed. 200 ul PEG (MW: 200) was added and mixed well. The mixture was then added with 1 ml varnish and mixed well. The color of the mixture was slightly red. The mixture was applied to a piece of spunbond coated polyethylene film and air-dried to show slightly pink color. The film became intensely pink upon in contact with water or synthetic urine. Using PEG (MW: 1000) to replace PEG (MW: 1000) resulted in the film that did not change upon wetting.

Example 10

Five vials, each containing 500 µl of crystal violet lactone (12 mg/ml) in ethanol and 500 ul of biphenol A (50 mg/ml) in ethanol and 500 µl of organic-solvent based varnish (from Sunchemical). In addition, 18 mg, 30 mg, 60 mg, 120 mg, 120 mg of polyethylene glycol (MW: 200) was added to vial 1, 2, 3, 4 and 5, respectively. To vial 5, 100 µl of benzethonium cloride in ehtanol was added. The mixtures were bath-sonicated for 5 minutes. A small amount of each mixture was applied to a polypropylene film to form a thin film. The films were air dried. The color of the film from vial 1, 2, 3, 4, and 5 are slightly blue, slightly blue, trace of blue, colorless and colorless, respectively. The color of the film formed by the mixture in vial 1, 2, 3, 4 and 5 all changed to blue upon in contact with synthetic urine.

Example 11

Five vials, each containing about 500 µl of crystal violet lactone (12 mg/ml) in ethanol and 500 ul of biphenol A (50 mg/ml) in ethanol and 500 µl of organic-solvent based varnish (from Sunchemical). In addition, 18 mg, 30 mg, 60 mg, 120 mg, 120 mg of polyethylene glycol (MW: 200) was added to vial 1, 2, 3, 4 and 5, respectively. To vial 5, 100 µl of benzethonium cloride in ehtanol was added. The mixtures were bath-sonicated for 5 minutes. A small amount of each mixture was applied to a polypropylene film to form a thin film. The films were air dried. The color of the film from vial 1, 2, 3, 4, and 5 are slightly blue, slightly blue, trace of blue, colorless and colorless, respectively. The color of the film formed by the mixture in vial 1, 2, 3, 4 and 5 all changed to blue upon in contact with synthetic urine.

The present invention has been described both generally and in detail by way of examples and the figures. Persons skilled in the art, however, can appreciate that the invention is not limited necessarily to the embodiments specifically disclosed, but that substitutions, modifications, and variations may be made to the present invention and its uses without departing from the spirit and scope of the invention. Therefore, changes should be construed as included herein unless the modifications otherwise depart from the scope of the present invention as defined in the following claims.

I claim:

1. A color-changing article comprising:
a substrate; and
a film disposed on a surface of the substrate, the film comprising a dried colorless or pale, non-aqueous based, homogeneous solution located in a water-pervious, organic polymeric cage comprising at least one polymer soluble in volatile organic solvents;
wherein the solution comprises a) one or more leuco dyes; b) one or more separators that are non-volatile and soluble in both volatile organic solvents and water; and c) one or more electron withdrawing color-developers that cannot form colored complexes with said leuco dyes in the presence of said separators without the presence of water, but can form colored complexes with the leuco dyes in the presence of water;
wherein the film manifests a color when contacted by an aqueous medium.

2. The article of claim 1, wherein the aqueous medium is an aqueous solution or urine.

3. The article of claim 1, wherein the substrate is selected from the group consisting of cellulose based tissue, cellulose-based paper, nonwoven material, breathable film, plastic film, polyethylene film, polypropylene film, and a combination thereof.

4. An absorbent article formed with the article of claim 1, wherein the absorbent article is a diaper, feminine hygiene pad, adult incontinence article, or wiper cloth.

5. The article of claim 1 wherein the film forms a pattern.

6. The article of claim 1 wherein the polymer is selected from a group consisting of an acrylate/acrylamide copolymer, a polyurethane adhesive, a vinylpyrrolidone copolymer, a dimethyl aminopropyl methacrylamide copolymer, a mono-alkyl ester of poly(methyl vinyl ether/maleic acid) copolymer, an acrylate/octoacrylamide copolymer, and a combination thereof.

7. The article of claim 1 wherein the polymeric cage comprises a polymeric resin.

8. The article of claim 1 wherein the one or more leuco dyes are selected from the group consisting of phthalide leuco dyes, triarylmethane leuco dyes, and fluoran leuco dyes.

9. The article of claim 1 wherein the one or more separators include neutral components without a charge.

10. The article of claim 1 wherein the one or more separators are selected from the group consisting ofinclude: polyalkylene glycol of <1000 Daltons, polyalkylene oxide of <10000 Daltons, block copolymers of polyoxyethylene polyoxypropylene glycol, polyoxyethylene nonylphenyl ether, polyoxyethylene distyrenated phenyl ether, and neutral surfactants.

11. The article of claim 1 wherein the color-developers are selected from the group consisting of include bisphenol A, zinc chloride, zinc salicylate, and phenol resins.

* * * * *